(12) United States Patent  (10) Patent No.: US 7,850,610 B2
Ferek-Petric  (45) Date of Patent: Dec. 14, 2010

(54) ELECTRODE LOCATION MAPPING SYSTEM AND METHOD

(75) Inventor: Bozidar Ferek-Petric, Zagreb (HR)

(73) Assignee: Medtronic, Inc., Minneapolis, MN (US)

( * ) Notice: Subject to any disclaimer, the term of this patent is extended or adjusted under 35 U.S.C. 154(b) by 1249 days.

(21) Appl. No.: 10/878,780

(22) Filed: Jun. 28, 2004

(65) Prior Publication Data

US 2005/0288586 A1 Dec. 29, 2005

(51) Int. Cl.
*A61B 8/00* (2006.01)
(52) U.S. Cl. .................................... 600/439
(58) Field of Classification Search ................ 600/300, 600/407, 408, 437–461; 601/2–4; 604/19, 604/20; 73/310
See application file for complete search history.

(56) References Cited

U.S. PATENT DOCUMENTS

| | | | |
|---|---|---|---|
| 4,264,312 A | 4/1981 | Cianci | 434/262 |
| 4,697,595 A | 10/1987 | Breyer et al. | 128/660 |
| 4,706,681 A | 11/1987 | Breyer et al. | 128/642 |
| 5,042,486 A | 8/1991 | Pfeiler et al. | 128/65 R |
| 5,297,549 A | 3/1994 | Beatty et al. | 128/642 |
| 5,409,000 A | 4/1995 | Imran | |
| 5,697,377 A * | 12/1997 | Wittkampf | 600/374 |
| 5,840,030 A * | 11/1998 | Ferek-Petric et al. | 600/439 |
| 5,879,297 A | 3/1999 | Haynor et al. | 600/407 |
| 5,944,022 A | 8/1999 | Nardella et al. | 128/899 |
| 5,954,649 A | 9/1999 | Chia et al. | 600/424 |
| 6,038,468 A | 3/2000 | Rex | 600/424 |
| 6,104,944 A | 8/2000 | Martinelli | 600/424 |
| 6,216,027 B1 * | 4/2001 | Willis et al. | 600/424 |
| 6,226,543 B1 | 5/2001 | Gilboa et al. | 600/407 |
| 2005/0131291 A1* | 6/2005 | Floyd et al. | 600/424 |
| 2007/0112272 A1* | 5/2007 | Park et al. | 600/461 |

FOREIGN PATENT DOCUMENTS

WO WO9905971 2/1999

* cited by examiner

*Primary Examiner*—Brian Casler
*Assistant Examiner*—Elmer Chao
(74) *Attorney, Agent, or Firm*—Carol F. Barry

(57) ABSTRACT

A mapped location of one or more electrodes within an electrical mapping volume is superimposed onto an ultrasound image corresponding to the electrical mapping volume.

16 Claims, 7 Drawing Sheets

ELECTRODE LOCATION MAPPING SYSTEM AND METHOD

FIELD OF THE INVENTION

The present invention relates generally to systems and methods for mapping an electrode position within a body, and more specifically to a system and method for superimposing an electrically mapped location of one or more electrodes onto a corresponding ultrasound image.

BACKGROUND OF THE INVENTION

The following background describes one context in which embodiments of the present invention may be practiced and should not be viewed as limiting the scope of the present invention as set forth in the appended claims.

Tachycardia is the condition of an accelerated pulse rate. Natural tachycardia occurs in physical exercise and emotional stress because of the sympathetic nervous tone and increase of the circulatory catecholamine concentration. The most important quality of natural tachycardia is the resultant increase in cardiac output. Pathologic tachycardia results in impaired hemodynamics, i.e. decreased cardiac output. The electrophysiology discriminates two major classes of tachycardia: supra-ventricular and ventricular, as well as two major classes of etiology: ectopic focuses and reentry phenomena. The therapy of tachycardia is in principle either the suppression of ectopic focuses or interruption of the reentry pathway. The first approach is always the pharmacotherapy. Despite of the recent advances in electropharmacology, every antiarrhythmic drug is not effective in every patient. Drugs also provoke side effects, which can be hazardous to the patient. Therefore more invasive modes of therapy must be considered like surgical treatment and permanent implantation of an electrotherapy device. One therapy of choice is cardiac ablation, which is a semi-invasive interventional method.

Transvenous catheter ablation of cardiac conduction tissue is a low risk alternative to surgical ablation to treat refractory supra-ventricular tachyarrhythmias. Some positive results have also been achieved in the treatment of ventricular tachycardia. The principal energy source for catheter ablations is a DC energy pulse from a standard defibrillator. In order to minimize the energy for the purpose of safety, numerous modifications in design of the energy source as well as of the catheter have been realized. In order to achieve the controllability of the lesion size as well as to avoid hazardous shock wave, the radiofrequency energy source has been introduced. For the same reason, laser ablation fiber optic catheters have been developed. The application of microwave energy is an alternative method, as well as ablation by means of chemical agents.

One of the challenges in to a clinician in performing an ablation procedure is the exact positioning of the ablation electrode within the heart. The positioning is normally observed under of radiographic imaging. Limitations of X-ray methods, however, include poor imaging of soft tissues, i.e. papillary muscle, interventricular septa, and so forth. As an alternative, ultrasonic imaging is well suited for imaging of soft tissues. Ultrasonically marked catheters and cardiac pacing leads have been described in U.S. Pat. No. 4,697,595 (Breyer, et al.) and in U.S. Pat. No. 4,706,681 (Breyer, et al.) respectively. Such systems enable the echocardiography guidance of the procedure for deploying a lead as well as the exact localization of the lead tip. If an ultrasonic transducer marks an ablation electrode, the exact position of the ablation electrode can be identified. A system having an ultrasonically marked cardiac ablation electrode wherein the ultrasonic sensitivity characteristics may be either in the same direction as the ablation field or in some other direction is disclosed in U.S. Pat. No. 5,840,030 (Ferek-Petric et al.), which is incorporated herein by reference in its entirety. The system allows radial orientation of the ultrasonically marked catheter as wells as directional field ablation.

Electrophysiologists usually monitor the intracardiac potentials to confirm the proper position as well as the proper contact of the electrode with the endocardium. However, the intracardiac potential is discontinuous being characterized with intrinsic deflection, which is repetitive at the frequency of the heartbeats. Distinct ST elevation caused by the injury current confirms the pressure of the electrode to the cardiac muscle. However, dislodgement may also occur anywhere within the cardiac cycle while there is no intracardiac signal. Ultrasonic imaging of the cardiac tissues and an ultrasonically marked ablation catheter allow the distance between the tissue and the ablation electrode to be measured as disclosed in the above-incorporated Ferek-Petric patent.

Although three-dimensional ultrasonic imaging is available, the currently high cost of three-dimensional systems generally prohibits widespread use. Therefore, even with the assistance of ultrasonically marked catheter, the catheter position is generally displayed in two dimensions. The clinician is required to envision the catheter position in three-dimensions, which makes exact positioning of the catheter a challenge. Three dimensional mapping systems have been proposed including the mapping system and method disclosed in U.S. Pat. No. 5,697,377 (Wittkampf et al.), which is incorporated herein by reference in its entirety. In this system, a catheter is provided with at least one measuring electrode. A voltage is measured between the measuring electrode and a reference electrode, which voltage signal has components corresponding to three orthogonal current signals applied to the patient substantially in the area to be mapped, such as the heart. The three-dimensional location of the catheter within the patient's body may be determined from the measured voltage signal components. This three-dimensional location may be represented relative to reference points on a graphic user interface. Without an anatomical image, however, the clinician must still envision the three-dimensional location of the catheter with respect to the patient's anatomy.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and.

DETAILED DESCRIPTION OF THE PREFERRED EMBODIMENTS

The following detailed description is exemplary in nature and is not intended to limit the scope, applicability, or configuration of the invention in any way. Rather, the following description provides a practical illustration for implementing exemplary embodiments of the invention.

Figure 1:
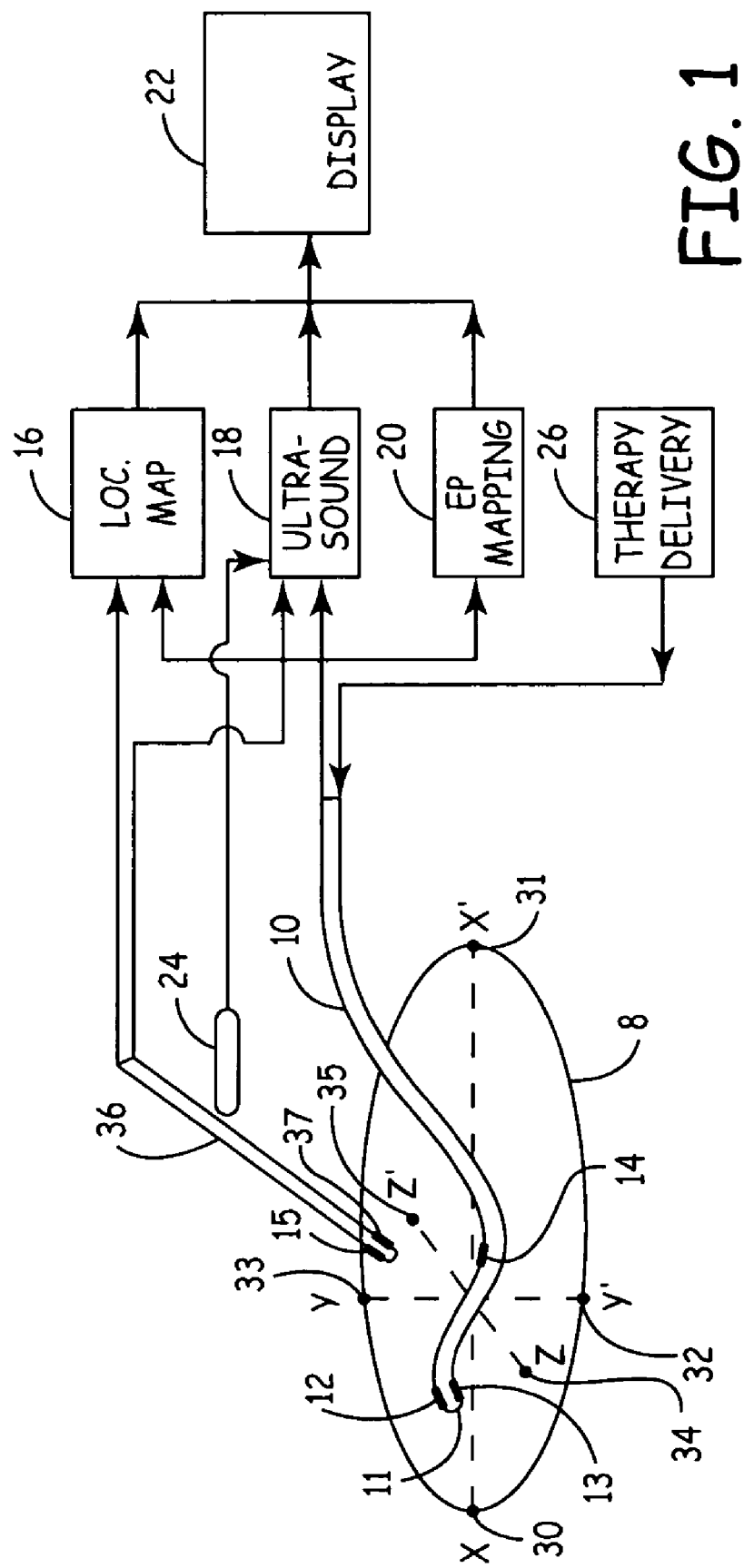
FIG. 1 is a schematic diagram of a mapping system in accordance with one embodiment of the present invention.

FIG. 1 is a schematic diagram of a mapping system in accordance with an embodiment of the present invention. The mapping system includes a measuring catheter 10 which may be mapped in three dimensions and used for delivering a medical therapy; a reference catheter 36 used in a calibration procedure for aligning ultrasound views and location mapping views; orthogonally-arranged electrodes 30, 31, 32, 33, 34, and 35 defining a local coordinate system of a mapping volume 8; and an ultrasound scanning probe 24. The measuring catheter 10, one or more reference catheters 36, orthogonally-arranged electrodes 30 through 35, and ultrasound scanning probe are coupled to appropriate components included in the mapping system, specifically a location mapping unit 16, an ultrasound imaging unit 18, an optional electrophysiological mapping unit 20, an optional therapy delivery unit 26, and an image display 22.

The anatomical volume of interest in a patient is indicated as mapping volume 8, which may correspond to a patient's heart. Mapping volume 8 illustrated in FIG. 1 is defined by orthogonal coordinates, X, Y, and Z wherein pairs of electrodes, 30 and 31, at locations X and X', 32 and 33, at locations Y and Y', and 34 and 35, at locations Z and Z', such that signal sources included in catheter location mapping circuitry 16 transmit a signal in each of the three orthogonal directions through mapping volume 8. Signal sources and measurement circuitry included in location mapping unit 16 may correspond to the mapping system disclosed in the previously-incorporated '377 patent (Wittkampf).

FIG. 1 illustrates catheter 10, having an elongated body, advanced into mapping volume 8. Catheter 10 may be a transvenous cardiac ablation catheter, the system and methods described herein expected to be particularly beneficial in cardiac ablation applications wherein precise positioning of the ablation catheter is critical to therapy success. However, the system and methods described herein may be beneficial in a number of other applications, particularly medical applications wherein a catheter- or lead-based therapy, such as an electrical therapy, a chemical or pharmacological therapy, or a genetic or other biological therapy, requires precise positioning of the catheter or lead delivering the therapy.

As illustrated in FIG. 1, catheter 10 includes a measuring electrode 12 positioned at or near a distal catheter tip 11 and a calibration electrode 14 spaced apart, proximally, from electrode 12. Calibration electrode 14, positioned at a known distance from measuring electrode 12, is used in a calibration procedure for determining coefficients in equations which define measured voltage signal components in the x, y and z directions as functions of the x, y, and z coordinate values for the location of measuring electrode 12. Details regarding the location mapping calibration procedure are provided in the aforementioned '377 Wittkampf patent.

Figure 3:
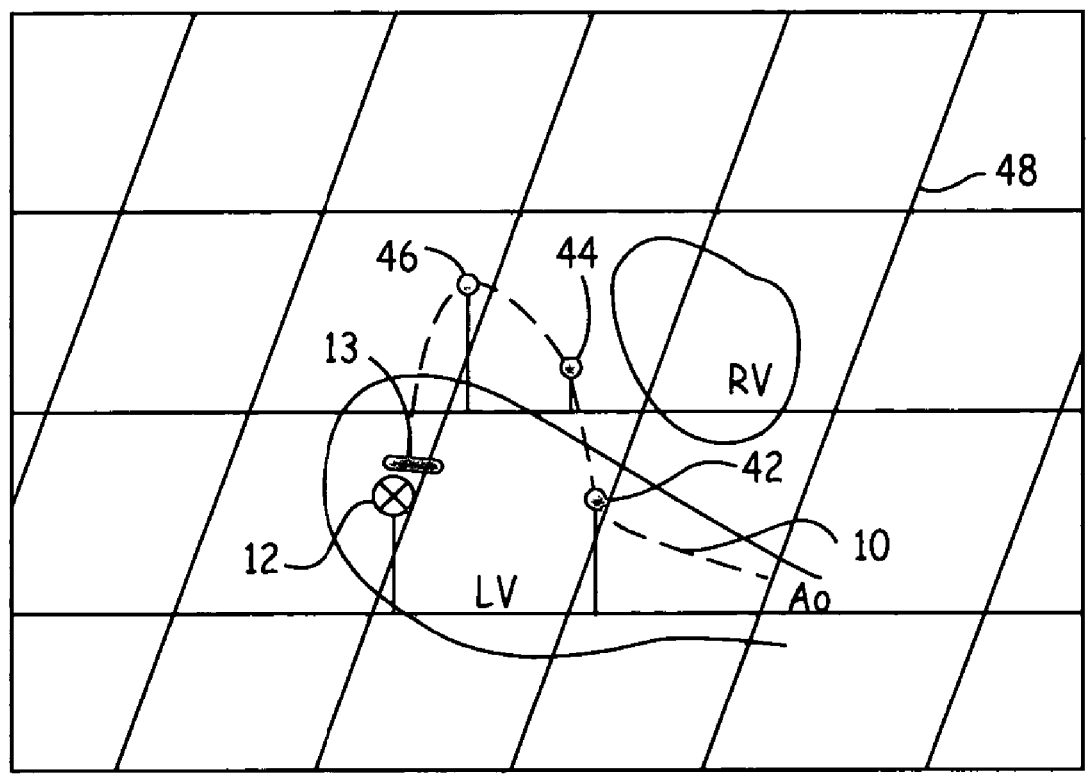
FIG. 3 is an schematic of a display of mapped catheter points superimposed on a 2-D ultrasound image according to one embodiment of the present invention.

Although just two electrodes 12 and 14 are shown for the sake of illustration, catheter 10 may further include three, four or more electrodes, i.e. further including electrodes 42, 44 and 46 illustrated in FIG. 3, so long as at least one electrode, i.e. measuring electrode 12, is included, preferably at or near the catheter tip 11, and a pair of electrodes, i.e. electrodes 12 and 14, separated by a known distance is included for location mapping calibration purposes. Measuring electrode 12 serves as a mapping electrode for mapping the three dimensional location of catheter tip 11 within mapping volume 8 by measuring a signal between measuring electrode 12 and a reference electrode 15. FIG. 1 illustrates reference catheter 36 including reference electrode 15, which is preferably anchored at a fixed location within mapping volume 8.

According to some embodiments of the present invention, three electrical signals are applied at slightly different frequencies or phases to respective orthogonal electrode pairs 30 and 31, 32 and 33, and 34 and 35 by location mapping unit 16. By adjusting a distinguishing characteristic, such as phase or frequency, for each of the three signals, a voltage signal measured between measuring electrode 12 and reference electrode 15 can be separated out as respective x, y, and z signals. Knowing the calibration coefficients obtained previously in the location mapping calibration procedure, the location of measuring electrode 12 may be derived from the measured voltage signal in orthogonal coordinates. Other two- or three-dimensional mapping techniques may be used to derive the location of one or more electrodes or other mapping elements located on catheter 10. Systems employing electrical signal measurements, such as current, voltage, impedance, or the like, electromagnetic, acoustic or other energy signal measurements from mapping elements positioned on a catheter may be substituted. For example, locating or positioning techniques that may be adapted for use with the present invention are disclosed in U.S. Pat. No. 5,944,022 issued to Nardella et al., U.S. Pat. No. 5,042,486 issued to Pfeiler et al., U.S. Pat. No. 6,104,944 issued to Martinelli, U.S. Pat. No. 5,879,297 issued to Haynor et al., or U.S. Pat. No. 6,226,543 issued to Gilboa et al., all of which patents are incorporated herein by reference in their entirety.

Measuring electrode 12 may additionally be used to measure cardiac depolarization signals for electrophysiological mapping purposes. As such, catheter 10 may be further coupled to electrophysiological (EP) mapping unit 20 to allow three-dimensional EP mapping to be performed using any of the catheter electrodes 12 and 14. Electrophysiological mapping apparatus and methods are known in the art.

When measuring catheter 10 is positioned as desired, an ablation electric field may be generated via electrode 12 to perform cardiac ablation under the control of therapy delivery unit 26. Alternatively, separate ablation and measuring electrodes for location and/or EP mapping may be provided on catheter 10. As noted previously, in alternative embodiments therapy delivery unit 26 may be used to control the delivery of other types of electrical or chemical therapies. Measuring catheter 10 thus serves as a therapy delivery catheter but is referred to herein as the "measuring" catheter in contrast to the "reference" catheter used for making location mapping measurements.

FIG. 1 further illustrates measuring catheter 10 including an ultrasonic marking transducer 13, located in close proximity to electrode 12, and reference catheter 36 including a reference ultrasonic marking transducer 37 located in close proximity to reference electrode 15. Ultrasound markers 13 and 15 may take the form of the transducer assembly disclosed in the '030 Ferek-Petric patent. Measuring catheter 10 and reference catheter 36 each generate an ultrasonic field via ultrasound markers 13 and 37 respectively. As such, measuring catheter 10 and reference catheter 36 are additionally coupled to ultrasound unit 8 to allow an ultrasound field to be generated in a desired direction. Ultrasound scans of a two-dimensional plane within mapping volume 8 may be acquired using an ultrasound probe 24, such as a trans-esophageal probe, to obtain a two dimensional image of the anatomy. An ultrasound scanning plane within mapping volume 8 is defined relative to a location mapping plane by means of ultrasound markers 13 and 37; arming of ultrasound scanning planes with the location mapping coordinate system, by alignment of an initial scanning plane with a location mapping reference plane, is performed in a calibration procedure to be described herein below.

The present invention may be practiced with the use of three-dimensional ultrasound scanning equipment as it becomes more widely used, however, the benefits of the present invention may be realized with the use of a less costly two-dimensional ultrasound system, which provides a two-dimensional anatomical view allowing an operator to determine a distance between electrode 12 and a cardiac structure. Display 22, i.e. a GUI, illustrated in FIG. 1, merges the location mapping, anatomical ultrasound image, and, optionally, EP mapping information into a single visual image, preferably a video image, to assist the operator in ascertaining a position of electrode 12 relative to anatomical structures. Display 22 receives output from location mapping unit 16, ultrasound unit 8, and optionally EP mapping unit 20. Display 22 preferably displays a three-dimensional image of catheter 10 as derived from location mapping measurements performed by location mapping unit 16 superimposed on a two- or three-dimensional anatomical image obtained from ultrasound unit 8. The 3-D location mapping image and 2-D or 3-D anatomical image may also be superimposed on a three-dimensional EP mapping image obtained from EP mapping unit 20.

Figure 2:
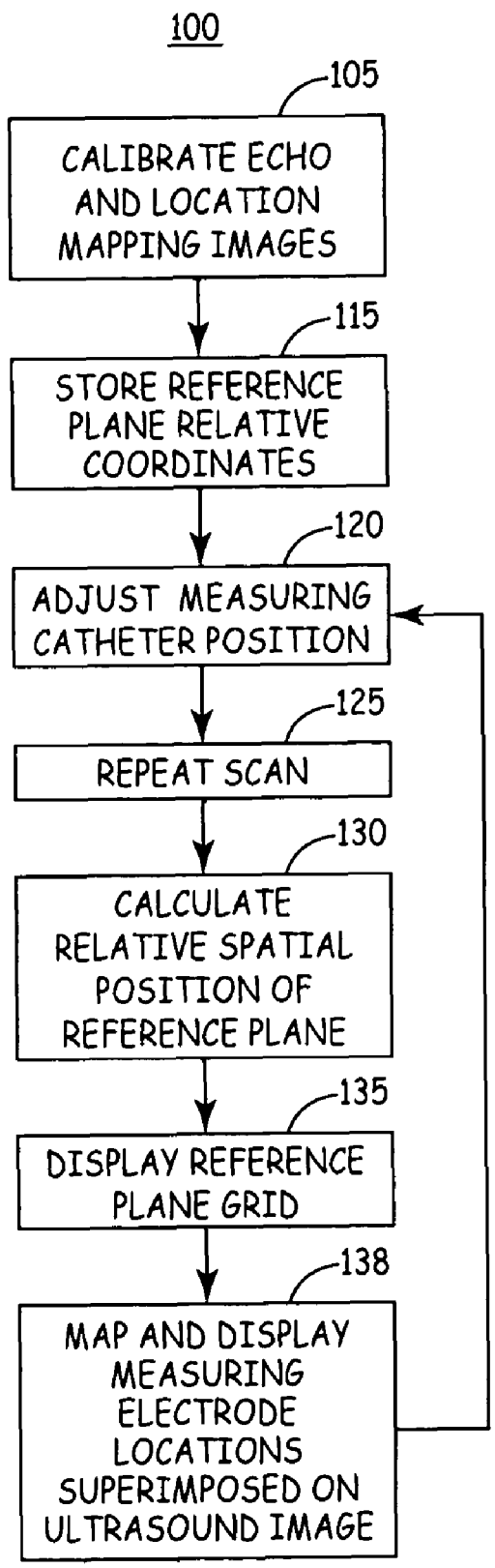
FIG. 2 is a flow chart summarizing the salient steps included in a method of the invention.

FIG. 2 is a flow chart summarizing the salient steps included in a method of the invention. At step 105, a calibration procedure is performed during which an ultrasound scanning plane and a location mapping reference plane are aligned. The reference plane coordinates within the local coordinate system of the location mapping system are then determined so that a relative position between new ultrasound scanning planes and the reference plane are known. These reference plane coordinates are stored at step 115. A calibration method performed at step 105 for arming the ultrasound and location mapping planes will be described in greater detail below.

At step 120, the position of measuring catheter 10 is adjusted, and then an ultrasound scan repeated at step 125; a resulting ultrasound image is displayed on the associated GUI or display 22 with a designated marker, e.g. a flashing signal, indicating the location of ultrasound marker 13 when it is in the ultrasound scanning plane. For each new ultrasound scan, the relative spatial position of the location mapping reference plane is calculated based on the stored relative coordinate system determined during calibration. At step 135, a perspective grid, i.e. grid 48 illustrated in FIG. 3, representing the location mapping reference plane is displayed, superimposed on the new two-dimensional ultrasound image to indicate a spatial angle between the ultrasound scanning plane and the location mapping reference plane. Then, at step 138, measuring catheter electrode locations, i.e. for electrodes 12, 42, 44, and 46 illustrated in FIG. 3, are mapped by the location mapping unit and marked relative to the reference plane coordinates on the GUI using designated markers, e.g. color-coded points. Steps 120 through 138 may be repeated until no further adjustments of the measuring catheter position are required. Ablation energy or another therapy may then be delivered at a selected site or sites.

FIG. 3 is a schematic of a display of mapped catheter points superimposed on a 2-D ultrasound image according to one embodiment of the present invention. The display shows measuring catheter 10 having been advanced into the left ventricle (LV) of the heart; an ascending aorta (Ao) and a right ventricle (RV) are also indicated. According to one embodiment, a flashing signal induced by ultrasound marker 13 indicates the location of measuring electrode 12 and unique symbol shape or color is used to mark locations of additional mapping electrodes 42, 44 and 46 included on measuring catheter 10. Grid 48 provides visualization of the location mapping reference plane, determined during the calibration procedure, with respect to the current ultrasound scanning plane; solid lines extending between the measuring electrode symbols and the reference plane grid 48 provide 3-D perspective visualization of locations of measuring electrodes 12, 42, 44, and 46 with respect to the reference mapping plane, while a dashed line joining the symbols indicates the approximate position of the catheter within the LV.

As measuring catheter 10 is advanced, ultrasound scans are repeated and, with each new ultrasound scan, the location mapping reference plane may be visualized by displaying reference plane grid 48 relative to the scanning plane. The relative angle between the ultrasound scan and the location mapping reference plane is calculated based on calibration results obtained previously, as will be described below. The electrode locations are then mapped and displayed relative to the reference plane grid 48, superimposed on the ultrasound image.

Figure 4:
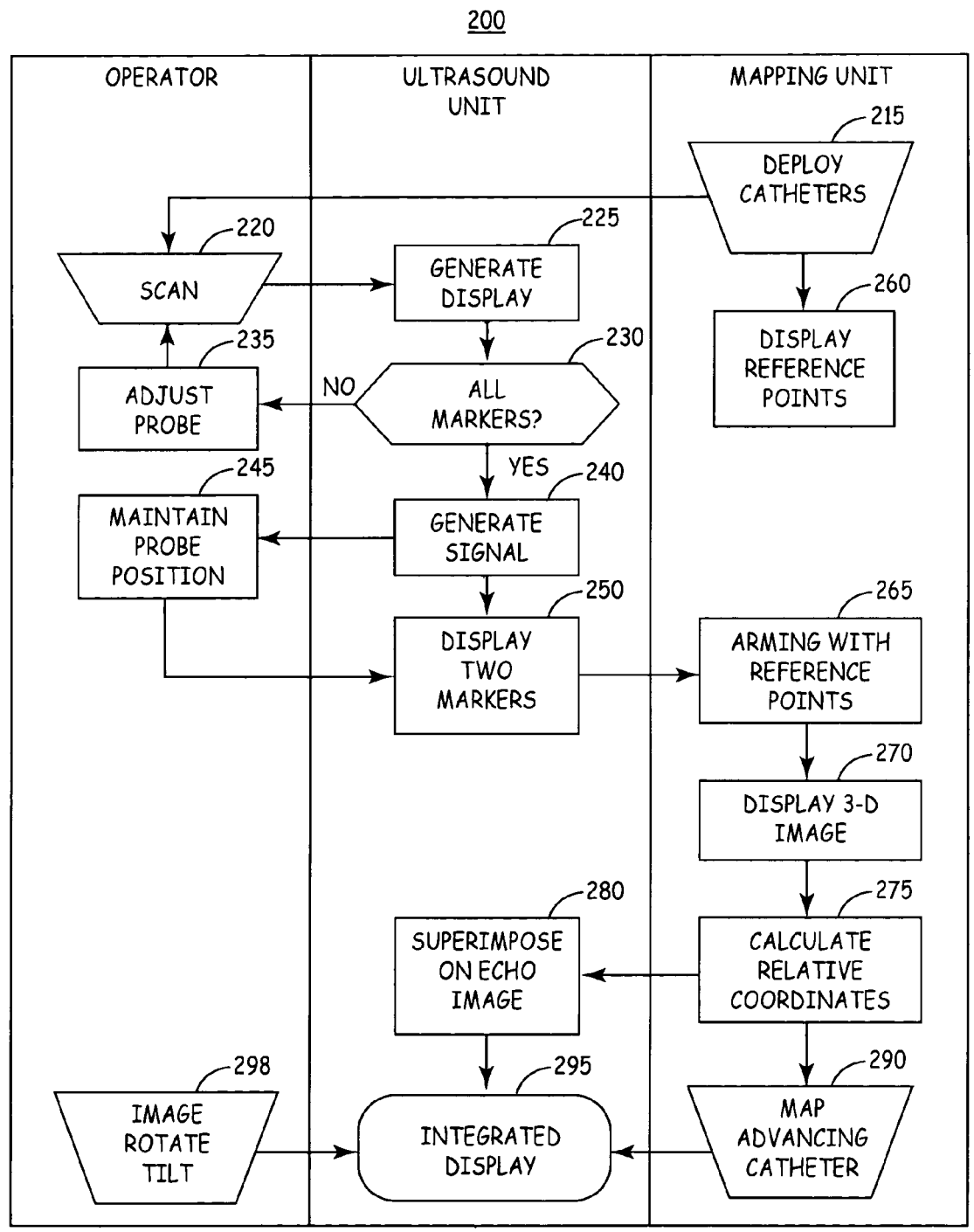
FIG. 4 is a flow chart providing an overview of steps included in a calibration method according to one embodiment of the present invention.

FIG. 4 is a flow chart providing an overview of steps included in a calibration method 200 for aligning three-dimensional location mapping catheter views with two-dimensional ultrasound views in a super-imposed image. Steps included in calibration method 200 are shown generally divided between steps performed by an operator, steps performed by an ultrasound unit included in the mapping system, and steps performed using the location mapping unit included in the mapping system. Method 200 begins at step 215 wherein a reference catheter and a measuring catheter are positioned in a mapping volume of interest. A three-dimensional view of the measuring and reference electrodes is displayed at step 260 using location mapping techniques. As described in conjunction with FIG. 1, each of the reference catheter and measuring catheter include at least one ultrasound marker located adjacent to the reference electrode and measuring electrode, respectively, used for performing location mapping measurements. According to an alternate embodiment, a single catheter is equipped with the measuring electrode and the reference electrode along with associated ultrasound markers to define a common plane between the location mapping world and the ultrasound imaging world.

In order to align a three-dimensional mapping image and a two-dimensional ultrasound image, the two electrodes and two ultrasound markers are positioned in the mapping volume to thereby define a common plane that may be identified by both the location mapping unit and the ultrasound imaging unit. At step 220, the operator performs an ultrasound scan of a plane within the mapping volume of interest, e.g. the heart. A two-dimensional ultrasound image is displayed at step 225 by image processing circuitry included in the ultrasound unit. The image processing circuitry determines if the at least two ultrasound markers are present in the ultrasound image at decision step 230. If not, the operator adjusts the ultrasound probe position at step 235 and returns to step 220 to perform a new scan. This process (steps 220 through 235) is repeated until both ultrasound markers are displayed in a single ultrasound image plane. Once the scanning plane defined by the two ultrasound markers is found, a signal is generated at step 240 notifying the operator so that he/she may maintain the ultrasound probe position at step 245. An audible or visual signal may be generated by the ultrasound unit to notify the operator that both ultrasound markers are within the imaging plane.

At step 250, the scanning view is displayed including a display of the two ultrasound markers, which may be visualized by a flashing light or other distinguishing icon. The scanning plane and the plane defined by the measuring and reference electrodes are now aligned. A small but expectedly acceptable error will be inherent in the alignment of the two planes since the ultrasound markers are not located in the exact same position as the measuring and reference electrodes. To minimize the calibration error, the ultrasound markers are preferably located as close as possible to the reference and measuring electrodes on the reference and measuring catheters, respectively.

Reference points defined by the reference and measuring electrodes and ultrasound markers may thus be registered in the separate two-dimensional ultrasound image and in the three-dimensional mapping image. As such, at step 265, the ultrasound scanning plane and the location mapping plane are armed together. The location of the ultrasound makers, which approximately coincide with the adjacent reference and measuring electrodes, are registered within the location mapping image. An updated three-dimensional image may be displayed at step 270 including individually identifiable markers indicating the reference and measuring electrode and ultrasound marker locations.

At step 275, the coordinates of the aligned scanning plane and location mapping reference plane are calculated relative to the three-dimensional location mapping coordinate world and stored within the operating memory of the system. The ultrasound image and the three-dimensional mapping image are then superimposed at step 280 to provide an integrated display at step 295.

The calibration procedures are now complete and the measuring catheter may be advanced within the mapping volume as indicated by step 290. New ultrasound scans (298) and location mapping images (290) are superimposed in the integrated display (295) as the catheter is advanced to a desired location. As described above in conjunction with FIG. 3, each updated display includes a reference grid indicating the angular position of the location mapping reference plane relative to the new ultrasound scanning plane and the measuring electrode locations are indicated by distinctive symbols or icons.

Figure 5A:
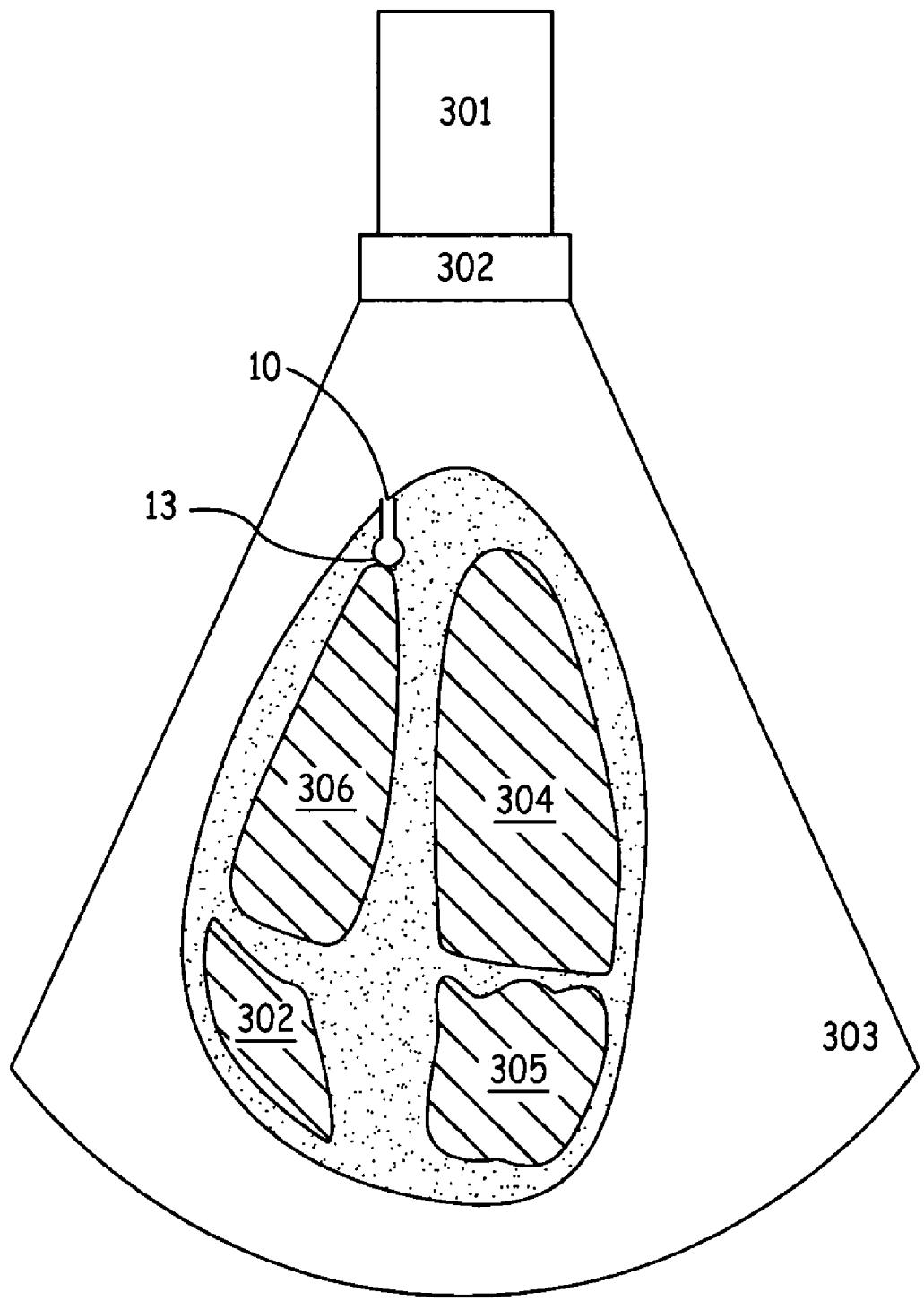
FIGS. 5A-C are schematics of two-dimensional four-chamber echocardiogram views of a patient's heart in which two ultrasonically-marked reference catheters have been placed.
Figure 5B:
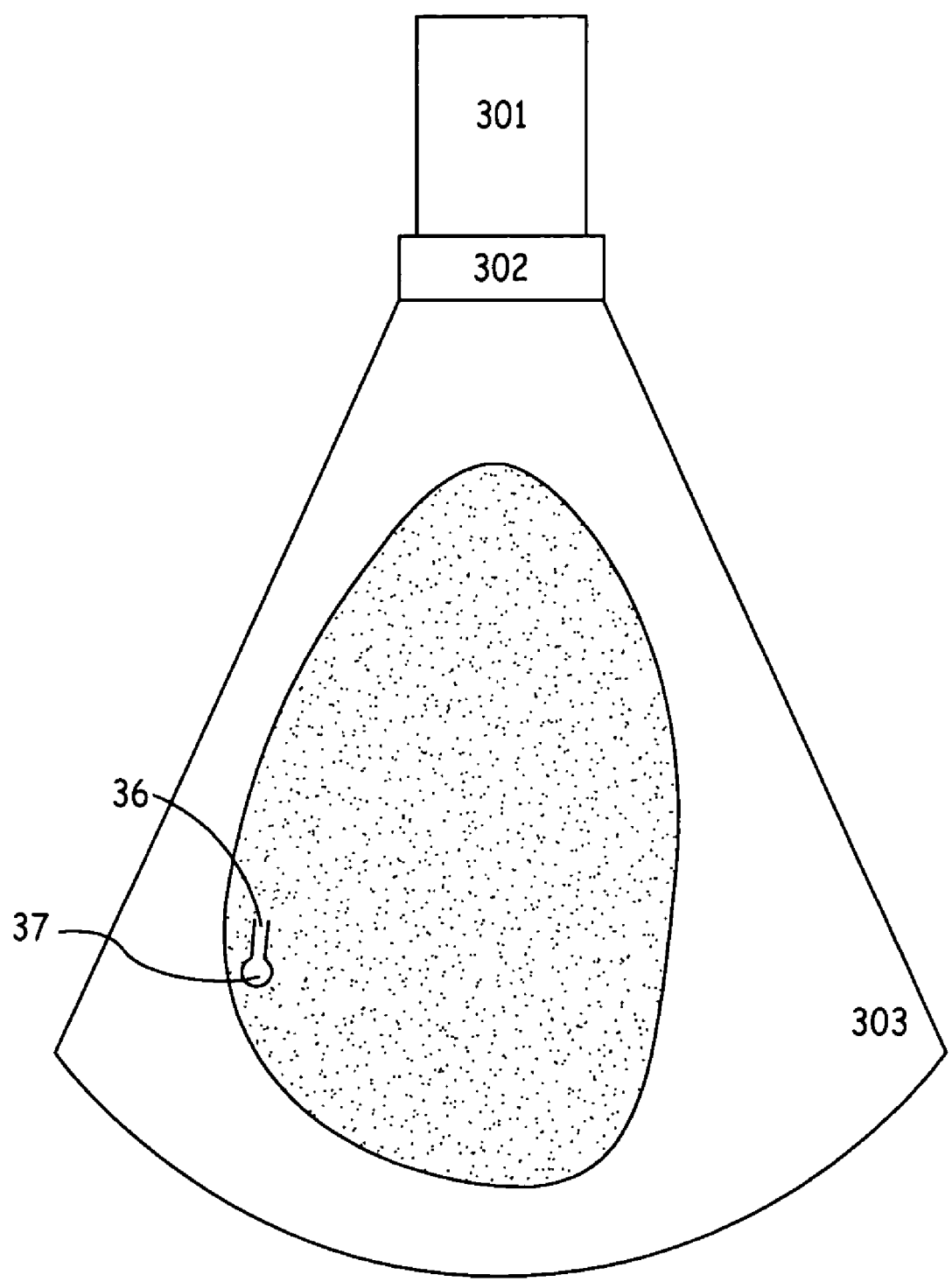
Figure 5C:
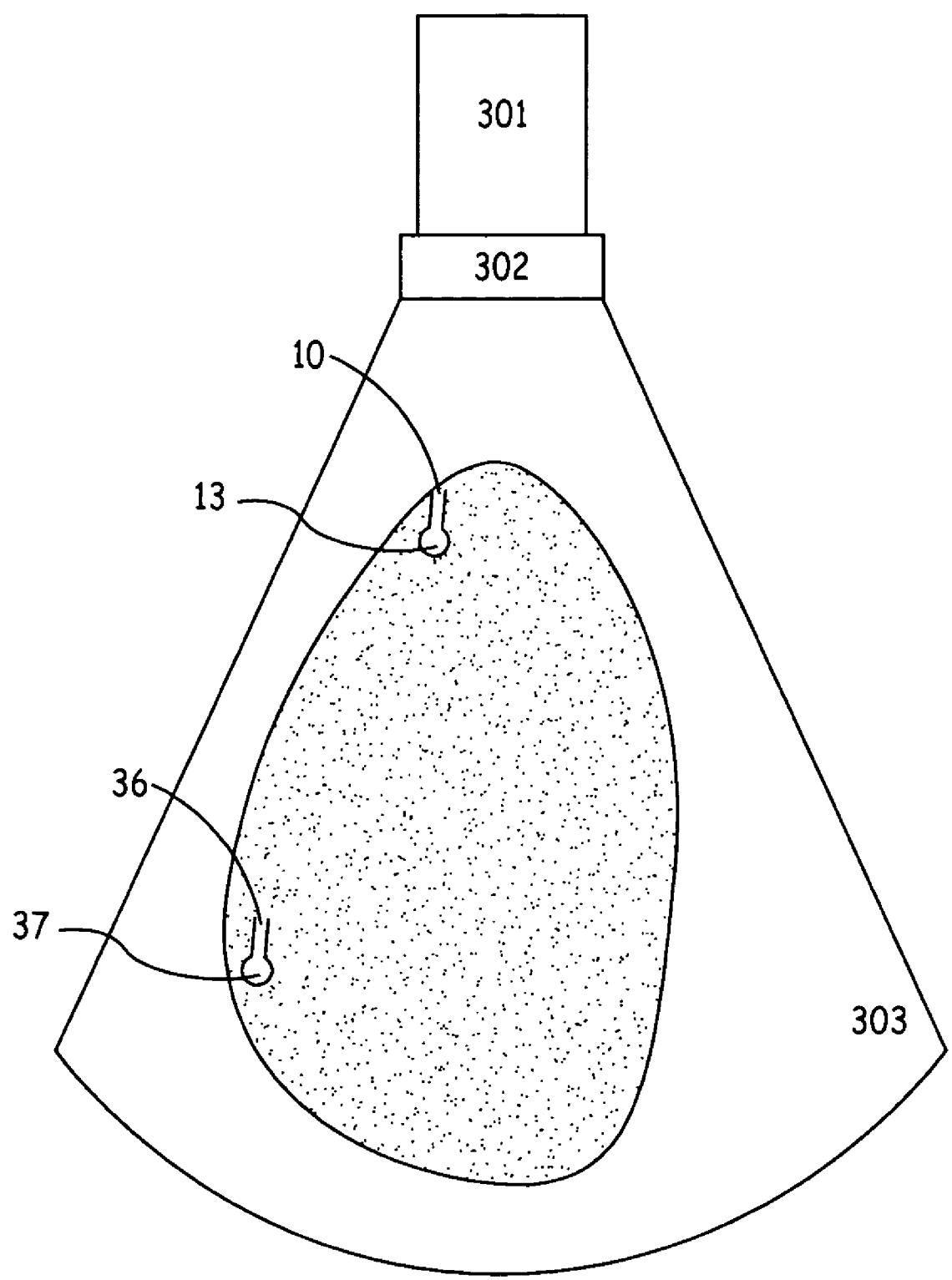

FIGS. 5A-C are schematics of two-dimensional four-chamber echocardiogram views of a patient's heart in which two ultrasonically-marked reference catheters have been placed. In FIG. 5A, the left ventricle 304, right ventricle 306, left atrium 305 and right atrium 307 are shown in a two-dimensional echocardiography scanning plane. A motor 301 is used to rotate the ultrasonic scanner probe 302. In the view shown in FIG. 5A, the ultrasound marker 13 located on measuring catheter 10 is visible as indicated by a flashing signal or other symbol or icon displayed in right ventricle 306. An operator can tilt the scanning probe 302 in order to change the angular orientation of scanning plane 303 relative to the patient's body surface. At a certain angular and polar position of scanner probe 302, both ultrasound markers 13 and 37 will appear in scanning plane 303 as shown in FIG. 5C. In a preferred embodiment, the ultrasound unit includes processing methods within image processing circuitry for detecting the appearance of two ultrasound markers within the image. When both ultrasound markers are detected, a signal is generated to alert the operator to maintain the probe 302 position and commence with mapping of relevant points, corresponding to the catheter electrodes, by the location mapping unit as described above in conjunction with method 200 shown in FIG. 4.

The calibration method 200 shown in FIG. 4 may also be applied in mapping systems including three-dimensional ultrasound imaging of the mapping volume. To obtain a three-dimensional image, the scanning plane 303 (FIGS. 5A through 5C) is rotated 180 degrees on the probe 302 axis. By arming the ultrasound scanning plane and location mapping image plane together at one ultrasound scanning plane that includes at least two ultrasound markers, the ultrasound and location mapping images may be integrated. The superimposed display of the three-dimensional ultrasound image and the location mapping image can be updated as new three-dimensional ultrasound views are obtained and/or the measuring catheter is advanced. The three-dimensional location mapping image including the distinctive symbols for each measuring electrode present may be observed moving through the three-dimensional ultrasound image. Display of a reference plane grid, as shown in FIG. 3, is not necessary for indicating the relative position of the ultrasound scanning plane to the reference plane since both the mapping image and the ultrasound image are displayed in three dimensions.

Thus, a mapping system has been described wherein a mapped location of one or more electrodes within an electrical mapping volume is superimposed on an ultrasound image corresponding to the mapping volume. The detailed descriptions provided herein are intended to be illustrative, not limiting, with regard to the following claims.

What is claimed is:

1. A medical device localization system, comprising:
   a plurality of orthogonally-arranged electrode pairs defining orthogonal planes extending through a mapping volume within a patient;
   a measuring electrode;
   an ultrasound marking transducer located in close proximity to the measuring electrode;
   a calibration electrode spaced apart from the measuring electrode;
   a reference electrode spaced apart from the measuring electrode and the calibration electrode;
   a reference ultrasound marking transducer located in close proximity to the reference electrode;
   a location mapping unit adapted to define the mapping volume and to locate the measuring electrode within the mapping volume by measuring a voltage signal between the measuring electrode and the reference electrode in response to electrical signals applied to the plurality of orthogonally-arranged electrode pairs;
   an ultrasound unit adapted to generate an ultrasound image of the patient's anatomy within the mapping volume; and
   a display unit adapted to receive data from the location mapping unit and from the ultrasound unit and to superimpose the location of the measuring electrode onto the ultrasound image;
   wherein the relative location of a reference plane in the mapping volume with respect to the ultrasound image is established by aligning an initial ultrasound scanning plane with the reference plane in the mapping volume by adjusting the initial ultrasound scanning plane to include both of the ultrasound marking transducer and the reference ultrasound marking transducer, and wherein the display unit is configured to display the relative location of the reference plane with respect to an ultrasound scanning plane.

2. The localization system of claim 1, wherein the measuring electrode, the ultrasound marking transducer and the calibration electrode are all included on a single elongated medical device.

3. The localization system of claim 1, wherein the measuring electrode is further adapted for delivering ablation energy.

4. The localization system of claim 1, further comprising one or more additional measuring electrodes.

5. The localization system of claim 1, wherein the measuring electrode and the ultrasound marking transducer are both included on a single elongated medical device and aligned with one another along a longitudinal axis of the medical device.

6. The system of claim 1, wherein the display unit is configured to display a perspective visualization line extending between the reference plane and the mapped location of the measuring electrode superimposed onto the ultrasound image.

7. A method for superimposing a mapped location of one or more electrodes within an electrical mapping volume onto an anatomical ultrasound image corresponding to the electrical mapping volume, the method comprising:
   positioning a plurality of orthogonally-arranged electrode pairs defining orthogonal planes extending through the electrical mapping volume within a patient;
   inserting an elongated device into the electrical mapping volume, the elongated device including the one or more electrodes, a first ultrasound marking transducer and a measuring electrode, which is included in the one or more electrodes, positioned in close proximity to the first ultrasound marking transducer;
   inserting a second ultrasound marking transducer and a reference electrode into the electrical mapping volume, the second ultrasound transducer being positioned in close proximity to the reference electrode;
   scanning the electrical mapping volume using an ultrasound probe associated with an ultrasound unit to obtain a first anatomical ultrasound image of an initial ultrasound scanning plane extending through the electrical mapping volume;
   detecting the first and second ultrasound marking transducers using the ultrasound unit;
   aligning the initial ultrasound scanning plane with a location mapping reference plane, which corresponds to the measuring electrode and the reference electrode, in the electrical mapping volume by aligning the initial ultrasound scanning plane to include the positions of the first and second ultrasound marking transducers detected by the ultrasound unit;
   storing coordinates of the location mapping reference plane; repositioning the elongated medical device, thereby repositioning the first ultrasound transducer and the measuring electrode in the electrical mapping volume;
   adjusting the ultrasound probe to scan a second ultrasound scanning plane according to the repositioned first ultrasound transducer;
   mapping the location of the one or more electrodes within the electrical mapping volume, the mapping comprising measuring a voltage signal between the measuring electrode and the reference electrode in response to voltage signals applied between the orthogonally-arranged electrode pairs;
   calculating a spatial angle between the location mapping reference plane and the second ultrasound scanning plane in response to the mapped location of the one or more electrodes;
   generating a second anatomical ultrasound image corresponding to the second ultrasound scanning plane; and
   superimposing the mapped location of the one or more electrodes onto the second anatomical ultrasound image.

8. The method of claim 7, wherein the second ultrasound image corresponding to the second ultrasound scanning plane is a 2-D image and further comprising the step of superimposing a perspective grid, representing the location mapping reference plane, in conjunction with the mapped location of the one or more electrodes.

9. The method of claim 7, wherein the detected positions of the first and second ultrasound markers in the aligned initial ultrasound scanning plane are indicated by a signal from the ultrasound unit.

10. A method for calibrating an electrical mapping volume to an anatomical ultrasound scan, the method comprising:
   positioning a plurality of orthogonally-arranged electrode pairs defining orthogonal planes extending through the electrical mapping volume within a patient;
   inserting an elongated device into the electrical mapping volume, the elongated device including one or more electrodes, a first ultrasound marking transducer and a measuring electrode, which is included in the one or more electrodes, positioned in close proximity to the first ultrasound marking transducer;
   inserting a second ultrasound marking transducer and a reference electrode into the electrical mapping volume, the second ultrasound transducer being positioned in close proximity to the reference electrode;
   scanning the electrical mapping volume by means of an ultrasound probe associated with an ultrasound unit;
   detecting the first and second ultrasound marking transducers using the ultrasound unit;
   aligning an initial ultrasound scanning plane with a location mapping reference plane, which corresponds to the measuring electrode and the reference electrode, in the electrical mapping volume by aligning the initial ultrasound scanning plane to include positions of the first and second ultrasound marking transducers detected by the ultrasound unit; and
   storing coordinates of the location mapping reference plane.

11. A medical device location mapping system, comprising:
   a location mapping unit mapping a location of a medical device in a mapping volume within a patient, wherein the medical device comprises a measuring electrode operably coupled to the location mapping unit;
   a plurality of orthogonally-arranged electrode pairs defining orthogonal planes extending through the mapping volume within the patient, wherein the location mapping unit is configured to transmit signals from the plurality of orthogonally-arranged electrode pairs in each of the orthogonal planes defined by the plurality of orthogonally-arranged electrode pairs and to provide at least a measurement signal in response to the transmitted signals using the measuring electrode to map the location of the medical device;
   an ultrasound unit obtaining an ultrasound image of the patient's anatomy along a plane within the mapping volume; and a display unit displaying a superimposed image of the ultrasound image and the mapped location, the display unit using an angle between a reference plane of the mapping volume and the plane of the ultrasound image to display the superimposed image.

12. The system of claim 11, wherein the system further comprises a reference electrode spaced apart from the measuring electrode of the medical device, wherein the reference electrode is operably coupled to the location mapping unit, wherein the location mapping unit is configured to provide at least a measurement signal between the measuring electrode and the reference electrode in response to the transmitted signals to map the location of the medical device.

13. The system of claim 12, wherein the medical device further comprises a first ultrasound transducer located in close proximity to the measuring electrode, and wherein the system further comprises a second ultrasound transducer located in close proximity to the reference electrode, wherein the display unit is adapted to receive data from the location mapping unit and from the ultrasound unit, wherein the angle between the reference plane of the mapping volume and the plane of the ultrasound image is established by aligning an initial ultrasound scanning plane with the reference plane in the mapping volume by adjusting the initial ultrasound scanning plane to include both of the first ultrasound transducer and the second ultrasound marking transducer.

14. A method, comprising:
    mapping a location of a medical device in a mapping volume within a patient, wherein the medical device comprises a measuring electrode, and wherein mapping the location of the medical device in the mapping volume within the patient comprises:
        positioning a plurality of orthogonally-arranged electrode pairs defining orthogonal planes extending through the mapping volume,
        transmitting signals from the plurality of orthogonally-arranged electrode pairs in each of the orthogonal planes defined by the plurality of orthogonally-arranged electrode pairs, and
        providing at least a measurement signal in response to the transmitted signals using the measuring electrode to map the location of the medical device;
    obtaining an ultrasound image of the patient's anatomy along a plane within the mapping volume; and
    displaying a superimposed image of the ultrasound image and the mapped location, the displaying comprising:
        determining a reference plane in the mapping volume,
        determining an angle between the reference plane and the plane of the ultrasound image, and
        superimposing the mapped location of the medical device onto the ultrasound image to form the superimposed image using the determined angle between the reference plane and the plane of the ultrasound image.

15. The method of claim 14, wherein mapping the location of the medical device in the mapping volume within the patient further comprises providing at least a measurement signal between the measuring electrode and a reference electrode in response to the transmitted signals to map the location of the medical device.

16. The method of claim 15, wherein determining the reference plane in the mapping volume comprises obtaining an ultrasound image of the patient's anatomy along a plane within the mapping volume using:
    a first ultrasound transducer located in close proximity to the measuring electrode, and a second ultrasound transducer located in close proximity to the reference electrode.

* * * * *